US010675007B2

(12) United States Patent
Rosenzweig et al.

(10) Patent No.: US 10,675,007 B2
(45) Date of Patent: Jun. 9, 2020

(54) FREQUENCY COMPOUNDING IN ELASTICITY IMAGING

(71) Applicant: Siemens Medical Solutions USA, Inc., Malvern, PA (US)

(72) Inventors: Stephen Rosenzweig, Seattle, WA (US); Manoj Menon, Bellevue, WA (US); Seungsoo Kim, Sammamish, WA (US); Yassin Labyed, Maple Valley, WA (US); Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 220 days.

(21) Appl. No.: 15/133,122

(22) Filed: Apr. 19, 2016

(65) Prior Publication Data

US 2017/0296150 A1 Oct. 19, 2017

(51) Int. Cl.
*A61B 8/08* (2006.01)
*G01S 7/52* (2006.01)
*A61B 8/00* (2006.01)

(52) U.S. Cl.
CPC ............ *A61B 8/5269* (2013.01); *A61B 8/461* (2013.01); *A61B 8/485* (2013.01); *A61B 8/5253* (2013.01); *G01S 7/52022* (2013.01); *G01S 7/52042* (2013.01); *G01S 7/52077* (2013.01); *A61B 8/463* (2013.01); *A61B 8/488* (2013.01); *A61B 8/5207* (2013.01)

(58) Field of Classification Search
CPC ..... A61B 8/5269; A61B 8/5207; A61B 8/461; A61B 8/485; A61B 8/488
See application file for complete search history.

(56) References Cited

U.S. PATENT DOCUMENTS

| 2010/0004540 | A1 | 1/2010 | Thiele |
| 2010/0286516 | A1 | 11/2010 | Fan et al. |
| 2013/0345565 | A1* | 12/2013 | Fan .......................... A61B 8/08 600/442 |

(Continued)

FOREIGN PATENT DOCUMENTS

| CN | 101496728 A | 8/2009 |
| CN | 101563626 A | 10/2009 |
| CN | 102283679 A | 12/2011 |

(Continued)

OTHER PUBLICATIONS

Benson, J., Fan, L. Tissue Strain Analytics—a complete ultrasound solution for elastography. Siemens Healthcare White Paper, 2012.

(Continued)

*Primary Examiner* — Jonathan Cwern (57) ABSTRACT

For noise reduction in elasticity imaging, frequency compounding is used. Displacements caused by the acoustic radiation force impulse are measured using signals at different frequencies, either due to transmission of tracking pulses and reception at different frequencies or due to processing received signals at different sub-bands. The displacements are (a) combined to compound and the compounded displacements are used to determine elasticity or (b) are used to determine elasticity and the elasticities from information at the different frequencies are compounded.

6 Claims, 5 Drawing Sheets

(56) References Cited

U.S. PATENT DOCUMENTS

| | | | |
|---|---|---|---|
| 2015/0087976 A1* | 3/2015 | Fan | A61B 8/485 600/438 |
| 2016/0143617 A1 | 5/2016 | Ebbini et al. | |

FOREIGN PATENT DOCUMENTS

| | | | |
|---|---|---|---|
| CN | 102920482 A | 2/2013 | |
| CN | 105793729 A | 7/2016 | |
| KR | 20080024327 A | 3/2008 | |
| KR | 20110110473 A | 10/2011 | |
| KR | 20120102510 A | 9/2012 | |
| KR | 20140112453 A | 9/2014 | |
| WO | 2013017105 A1 | 2/2013 | |

OTHER PUBLICATIONS

Berg, Wendie A., et al. "Shear-wave elastography improves the specificity of breast US: the BE1 multinational study of 939 masses." Radiology 262.2 (2012): 435-449.

Cheng, Yangjie, et al. "Frequency compounding for ultrasound freehand elastography." Bioinformatics and Biomedical Engineering (iCBBE), 2010 4th International Conference on. IEEE, 2010: Abstract Only.

Elegbe, Etana C., and Stephen A. McAleavey. "Single tracking location methods suppress speckle noise in shear wave velocity estimation." Ultrasonic imaging 35.2 (2013): 109-125.

Foucher, Juliette, et al. "Diagnosis of cirrhosis by transient elastography (FibroScan): a prospective study." Gut 55.3 (2006): 403-408.

Hollender, Peter J., et al. "Single- and multiple-track-location shear wave and acoustic radiation force impulse imaging: Matched comparison of contrast, contrast-to-noise ratio and resolution." Ultrasound in medicine & biology 41.4 (2015): 1043-1057.

Mariappan, Yogesh K., Kevin J. Glaser, and Richard L. Ehman. "Magnetic resonance elastography: a review." Clinical anatomy 23.5 (2010): 497-511.

McAleavey, Stephen A., Manoj Menon, and Jarrod Orszulak. "Shear-modulus estimation by application of spatially-modulated impulsive acoustic radiation force." Ultrasonic imaging 29.2 (2007): Abstract Only.

Nightingale, Kathryn R., et al. "On the feasibility of remote palpation using acoustic radiation force." The Journal of the Acoustical Society of America 110.1 (2001): 625-634.

Ophir, Jonathan, et al. "Elastography: a quantitative method for imaging the elasticity of biological tissues." Ultrasonic imaging 13.2 (1991): Abstract Only.

Palmeri, Mark L., et al. "A finite-element method model of soft tissue response to impulsive acoustic radiation force." Ultrasonics, Ferroelectrics, and Frequency Control, IEEE Transactions on 52.10 (2005): 1699-1712.

Palmeri, Mark L., et al. "Quantifying hepatic shear modulus in vivo using acoustic radiation force." Ultrasound in medicine & biology 34.4 (2008): 546-558.

Pinton, Gianmarco F., Jeremy J. Dahl, and Gregg E. Trahey. "Rapid tracking of small displacements with ultrasound." Ultrasonics, Ferroelectrics, and Frequency Control, IEEE Transactions on 53.6 (2006): 1103-1117.

Sanchez, Jose R., and Michael L. Oelze. "An ultrasonic imaging speckle-suppression and contrast-enhancement technique by means of frequency compounding and coded excitation." Ultrasonics, Ferroelectrics, and Frequency Control, IEEE Transactions on 56.7 (2009): Abstract Only.

Sarvazyan, Armen P., et al. "Shear wave elasticity imaging: a new ultrasonic technology of medical diagnostics." Ultrasound in medicine & biology 24.9 (1998): 1419-1435.

Trahey, Gregg E., et al. "A quantitative approach to speckle reduction via frequency compounding." Ultrasonic Imaging 8.3 (1986): Abstract Only.

Walker, William F., and Gregg E. Trahey. "A fundamental limit on delay estimation using partially correlated speckle signals." Ultrasonics, Ferroelectrics, and Frequency Control, IEEE Transactions on 42.2 (1995): 301308.

Zhai, Liang, et al. "Characterizing stiffness of human prostates using acoustic radiation force." Ultrasonic imaging 32.4 (2010): 201-213.

KR Office action dated Mar. 21, 2018 in KR Application No. 10-2017-0049729, English translation attached (22 pages).

Shaoguo Cui et al: "Noise reduction for ultrasonic elastography using transmit-side frequency compounding: a preliminary study"; IEE Transactions on ultrasonics; Ferroelectrics and frequency control; vol. 58; No. 3; 1. Mar. 2011; pp. 509-516; XP055558214; US; ISSN: 0885-3010; DOI: 10.1109/TUFFC.2011.1835 / Jan. 3, 2011.

Tsuyoshi Shiina et al: "WFUMB Guidelines and Recommendations for Clinical Use of Ultrasound Elastography: Part 1: Basic Principles and Terminology"; Ultrasound in Medicine Biology.; vol. 41; No. 5; 1. May 2015; pp. 1126-1147; XP055558278; US; ISSN: 0301-5629; DOI: 10.1016/j.ultrasmedbio.2015.03.009 / Jan. 5, 2015.

Jihoon Park et al: "Speckle reduction techniques in medical ultrasound imaging"; Biomedical Engineering Letters; vol. 4; No. 1; 1. Mar. 2014; pp. 32-40; XP055559515; Korea; ISSN: 2093-9868; DOI: 10.1007/s13534-014-0122-6 / Jan. 3, 2014.

Chinese Office Action dated Sep. 18, 2019 in corresponding Chinese Patent Application No. 201710256658.2.

\* cited by examiner

FREQUENCY COMPOUNDING IN ELASTICITY IMAGING

BACKGROUND

The present embodiments relate to elasticity imaging with ultrasound using acoustic radiation force (ARF). Ultrasound elasticity imaging includes different imaging techniques that characterize the elastic properties of tissue, such as acoustic radiation force impulse (ARFI) imaging or shear wave elasticity imaging (SWEI). These techniques characterize structure and/or pathology.

In ultrasound elasticity imaging techniques, a force is applied to tissue, and the resulting tissue displacement is measured in order to determine mechanical properties of the tissue. The induced displacements are typically small, on the order of 10 μm for ARFI. When estimating the displacement within the tissue, one major source of noise is the underlying speckle of the ultrasound signals used to estimate the motion. This noise may have a disproportionate effect in estimating given the small amount of displacement.

BRIEF SUMMARY

By way of introduction, the preferred embodiments described below include methods, instructions, and systems for noise reduction in elasticity imaging using acoustic radiation force. Frequency compounding is used. Displacements caused by the acoustic radiation force impulse are measured using signals at different frequencies, either due to transmission of tracking pulses and reception at different frequencies or due to processing received signals at different sub-bands. The displacements are (a) compounded and the compounded displacements are used to determine elasticity or (b) used to determine elasticity, and the elasticities from information at the different frequencies are compounded.

In a first aspect, a method is provided for noise reduction in elasticity imaging with an ultrasound scanner. A transducer of the ultrasound scanner transmits acoustic radiation force to tissue of a patient. The tissue responds to stress caused by the acoustic radiation force. The ultrasound scanner transmits a sequence of first ultrasound pulses having a first center frequency. The ultrasound scanner receives first ultrasound echoes responsive to the sequence of the first ultrasound pulses. The receiving of the first ultrasound echoes is interleaved with the transmitting of the first ultrasound pulses such that some of the first ultrasound echoes are received after each of the first ultrasound pulses and prior to the transmitting of a next of the first ultrasound pulses. The ultrasound scanner transmits a sequence of second ultrasound pulses having a second center frequency. The second center frequency is different than the first center frequency, and the second ultrasound pulses are transmitted in separate transmit events from the first ultrasound pulses. The ultrasound scanner receives second ultrasound echoes responsive to the sequence of the second ultrasound pulses. The receiving of the second ultrasound echoes is interleaved with the transmitting of the second ultrasound pulses such that some of the second ultrasound echoes are received after each of the second ultrasound pulses and prior to the transmitting of a next of the second ultrasound pulses. Displacements of the tissue over time at first and second frequency bands are determined from the first and second ultrasound echoes, respectively. An output elasticity is estimated from a combination of the displacements at the first and second frequency bands. An image of the output elasticity is generated.

In a second aspect, a method is provided for noise reduction in elasticity imaging with an ultrasound scanner. A transducer of the ultrasound scanner transmits acoustic radiation force to tissue of a patient. The tissue responding to stress caused by the acoustic radiation force. The ultrasound scanner transmits a sequence of transmit beams where each transmit beam has a frequency response with a single peak. The ultrasound scanner receives a sequence of receive signals in response to each of the transmit beams where the receiving of the receive signals is interleaved with the transmitting of the transmit beams. The ultrasound scanner determines tissue motions from different frequencies of the receive signals. The ultrasound scanner generates an image of elasticity where the image is based on the tissue motions at the different frequencies.

In a third aspect, a system is provided for noice reduction in elasticity imaging. A transmit beamformer is configured to transmit pulses. Each of the pulses has a single band with just one center frequency. A receive beamformer is configured to receive signals interleaved with the transmit pulses. A filter is configured to output information in different frequency bands for the received signals. A processor is configured to detect displacements of tissue responding to acoustic radiation force from the information in the different frequency bands and to generate elasticity from a compound of the different frequency bands. A display is configured to output the elasticity.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Frequency compounding is used in radiation force-based elasticity imaging. Frequency compounding provides noise reduction. Frequency compounding traditionally involves obtaining B-mode ultrasound signals with sufficiently different frequency spectra, performing envelope detection (a nonlinear operation), and finally re-combining the detected data.

For elasticity imaging, the frequency compounding occurs after the displacement determination. Two possible frequency-compounding techniques are proposed: transmit-receive and receive-only. The transmit-receive technique utilizes different frequencies on successive transmits before and after the displacement is induced within the tissue, resulting in receive signals at different frequency bands. The receive-only technique filters the radio frequency (RF) or in-phase and quadrature (IQ) data into multiple frequency bands after receiving the scattered echoes from transmissions at a single frequency. These two methods may be combined such that received signals for each of the different transmit frequencies are filtered into multiple receive frequency bands. Displacement is determined for each of the frequency bands. The displacements are then combined either immediately (e.g., averaging the initial displacement estimates) or after further imaging processing (e.g., generate shear velocity images for each frequency and take the median shear velocity value between the individual images).

Figure 1:
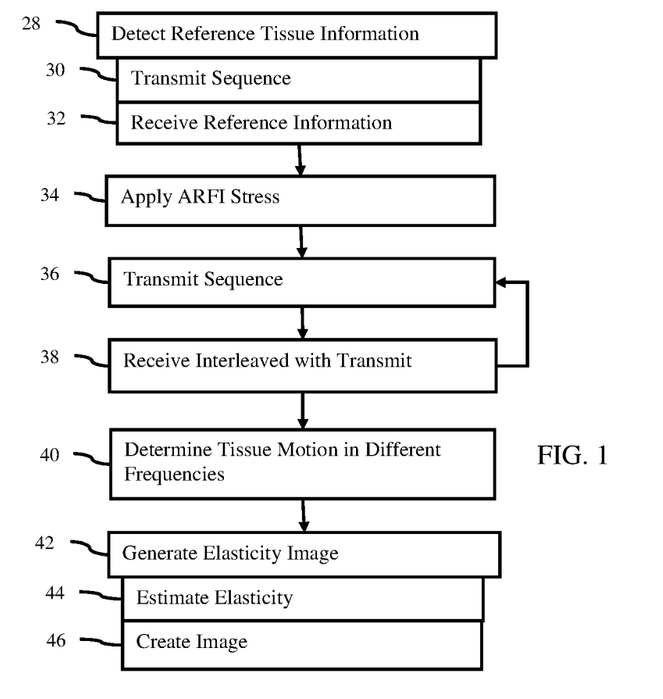
FIG. 1 is a flow chart diagram of one embodiment of a method for noise reduction in elasticity imaging.

FIG. 1 shows one embodiment of a method for noise reduction in elasticity imaging with an ultrasound scanner. Using any transmit and/or receive technique, receive signals at different frequency bands are created. Displacements are calculated for each frequency band. The displacements are combined, providing frequency compounding, and an elasticity image is estimated. Alternatively, elasticity images are estimated from the displacements at different frequency bands, and the images are combined, providing frequency compounding. The frequency compounding reduces the influence of speckle, providing better images of the patient and/or more precision in elasticity values.

Figure 7:
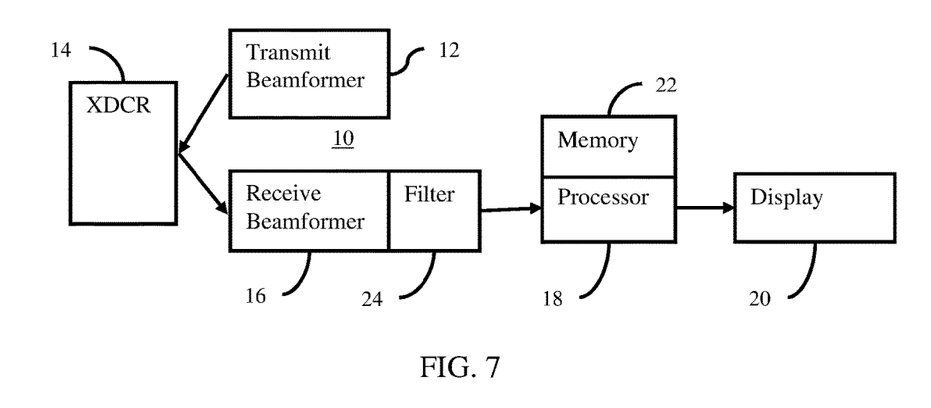
FIG. 7 is a block diagram of one embodiment of a system for noise reduction in elasticity imaging.

The method is implemented by the system of FIG. 7 or a different system. Transmit and receive beamformers use a transducer to transmit and receive from the patient, including applying ARFI and tracking the tissue response in acts 28-38. The tissue at the ARFI focus or tissue subjected to a shear wave spaced from the focus is tracked. A filter may isolate information at different frequency bands. An image processor determines the tissue motion and generates the elasticity image in acts 40 and 42. Different devices, such as other parts of an ultrasound scanner, may perform any of the acts.

Additional, different, or fewer acts may be provided. For example, acts 28, 30, and/or 32 are not performed. As another example, acts for configuring the ultrasound scanner, positioning the transducer, and/or recording results are provided.

The acts are performed in the order described or shown (i.e., top to bottom), but may be performed in other orders. For example, act 28 may be performed after act 38. As another example, acts 36 and 38 are performed in parallel or repeated (e.g., transmit, then receive, then transmit, then receive and so on).

In act 28, the ultrasound scanner detects reference tissue information. To determine the displacement caused by ARFI, the tissue at rest or not subjected to the ARFI is scanned. The scanning occurs prior to transmission of the ARFI in act 34, but may be performed at other times.

Acts 30 and 32 provide two examples of scanning for the reference information. In act 30, a sequence of pulses is transmitted to tissue prior to application of a stress and measurement of the tissue response to the stress. Since the tissue response to the stress may be measured before, after or both relative to the peak stress, the transmission for reference tissue position is performed prior to application of the stress or after the tissue returns to a relaxed state.

The sequence is the same as provided in act 36, such as being a sequence of pulses all having a same frequency band and center frequency or a sequence of pulses varying the frequency band and center frequency across the pulses. One set of N pulses is transmitted before ARFI is applied and is used to acquire reference data for displacement estimation. N may be any positive integer for each spatial location or group of spatial locations.

In act 32, reference information is received. Electrical signals generated by the transducer in response to echoes from the transmission are received. The signals are separated by frequency band, such as by filtering, demodulation and filtering, and/or receiving in response to transmissions at different frequency bands. For example, in-phase and quadrature (IQ) pairs of beamformed samples for each separable signal are generated.

The separated signals are used to detect reference tissue information. Any type of detection may be used, such as a B-mode detection of the intensity. The detected information is responsive to the transmitting prior to application of the stress in act 30. The tissue information is detected separately for different frequencies. Alternatively, tissue information is detected based on an average of different frequencies or based on one frequency. In other embodiments, the beamformed data without detection is used as the reference.

In act 34, the ultrasound scanner uses the transducer to apply stress to the tissue. For example, ARFI focused at the region of interest or a point is transmitted. When ARFI is applied to a focused area, the tissue responds to the applied force by moving. Relative to an original location or relaxed state, tissue is displaced. At each given spatial location, this displacement increases and then recovers to zero, resulting in a temporal displacement profile. The tissue properties affect the displacement.

The radiation force impulse may be generated by a cyclical pulsed waveform of any number of cycles (e.g., tens or hundreds of cycles). For example, ARFI is transmitted as a pushing pulse with 100-1000 cycles. The transmitted acoustic wave propagates to the region of interest, causing a deposition of energy and inducing tissue displacement.

Acts 36 and 38 occur after the radiation force is applied and while the tissue is responding to the stress. For example, transmission and reception occur after application or change in the stress and before the tissue reaches a relaxed state. The detection of motion in act 40 occurs in real-time with the reception of act 38. Alternatively, the detection of act 40 is performed from stored signals after the tissue reaches the relaxed state.

The response of tissue at scan lines for transmit or receive beams is detected. Doppler or B-mode scanning may be used for tracking the tissue responding to the stress. Ultrasound imaging is performed before, during and/or after the stress is applied. Ultrasound data is received in response to transmissions of ultrasound. The transmissions and receptions are performed for a single spatial location (e.g., a point adjacent to a focal point of the applied stress), along a line, over an area, or over a volume. A sequence of transmissions and receptions are provided for each spatial location to track over time. Using reception of multiple receive beams in response to each tracking transmission, data for a plurality of laterally spaced locations and/or depths may be received simultaneously.

In act 36 for tracking, the ultrasound scanner transmits a sequence of transmit beams. A plurality of ultrasound signals are transmitted to the tissue responding to the stress. The plurality of signals are transmitted in separate transmit events. A transmit event is a contiguous interval where transmissions occur without reception of echoes responsive to the transmission. During the phase of transmitting, there is no receiving. Where a sequence of transmit events is performed, a corresponding sequence of receive events is also performed in act 38. A receive event is performed in response to each transmit event and before the next transmit event.

For a transmit event, a transmit beam is formed. Each transmit beam has a frequency response. For example, a transmit beam is formed by a 2.0 MHz pulse of 2 cycles. The spectrum of the pulse provides an energy peak at 2.0 MHz with no other peaks within 10 or 20 dB down at another frequency. Any bandwidth may be provided.

The pulses to form the transmit beams are of any number of cycles. For example, three or more cycles may be used. A greater number of cycles may reduce the bandwidth of the pulses, allowing more complete frequency separation on receive. In one embodiment, each pulse is at least 4 cycles. Any envelope, type of pulse (e.g., unipolar, bipolar, or sinusoidal), or waveform may be used.

For frequency compounding, the sequence of transmit beams may all have a same center frequency and bandwidth. For example, each transmission in the sequence has a 2.0 MHz center frequency with a same pulse or bandwidth. The receive-only technique utilizes any standard pulse sequence for B-mode or other mode of ultrasound imaging.

The transmit-receive technique transmits the pulses with different frequency spectra. A repeating pattern of the different pulses is used. The multiple imaging pulses of the sequence may have different center frequencies. Any pattern of frequency change may be used, such as an every other or every third pattern. Any number of different transmit pulses may be used in the sequence, such as cycling between two different center frequencies or through three different center frequencies.

Figure 2:
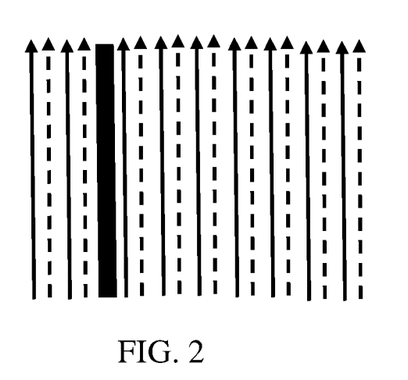
FIG. 2 illustrates an example sequence of transmit pulses with different frequencies.

FIG. 2 shows an example of a sequence of ultrasound pulses having two different center frequencies. Each solid arrow represents a transmit beam with a band around one center frequency (e.g., 1.5 MHz), and each dashed arrow represents a transmit beam with a band around a different center frequency (e.g., 2.25 MHz). The solid block represents the ARFI transmission of act 34, so FIG. 2 shows the sequence of transmit beams with alternating center frequency both before and after ARFI, such as implementing both of acts 30 and 36. Any number of transmit beams may be used before and/or after the ARFI. The bandwidth of the transducer may limit or determine the frequency separation and range of frequencies to be used.

The transmit-receive technique utilizes different frequencies on successive transmits before and after the displacement is induced within the tissue. This scheme may be expanded to N frequencies, with each frequency repeating on the $N^{th}$ transmit. In this method, the effective pulse repetition frequency (PRF) of the tracks is reduced by a factor of N for signals at one given frequency.

In act 38, the transducer receives ultrasound echoes in response to each transmit event. The transducer converts the echoes to receive signals, which are receive beamformed into ultrasound data representing one or more spatial locations. The ultrasound scanner receives a sequence of receive signals where receive beams are received in response to each of the transmit beams in the transmit sequence.

The reception is interleaved with the transmission of the sequence. For each transmit event, a receive event occurs. The receive event is a continuous interval for receiving echoes from the depth or depths of interest. The event occurs after ceasing the transmit event. After the transducer completes generation of acoustic energy for a given transmission, the transducer is used for reception of the responsive echoes. The transducer is then used to repeat another transmit and receive event pair for the same spatial location or locations, providing the interleaving (e.g., transmit, receive, transmit, receive, . . . ) to track the tissue response over time.

For the receive-only technique of frequency compounding, the receive signals are filtered into bands for different frequencies. The transmit beams of the sequence use the same center frequency and frequency band. The reception is performed at the same or similar frequency band and center frequency as used in transmit. To provide information at more than one frequency band, the receive band is separated into two or more sub-bands. The receive signals and/or beamformed samples are filtered to isolate information at different center frequencies and/or frequency bands. The receive-only technique utilizes a standard pulse sequence and filters the received ultrasonic echoes into narrower frequency bands. For example, the receive signals are at 1-3 MHz (center frequency of 2 MHz), so are filtered into two bands of 1-2 MHz (center frequency of 1.5 MHz) and 2-3 MHz (center frequency of 2.5 MHz).

The sub-bands in the example above do not overlap. Overlapping sub-bands may be used. Sub-bands separated by a range of frequencies may be used.

In the case of radio-frequency (RF) data, multiple band-pass filters are applied to the raw receive signals. For in-phase and quadrature (IQ) data, complex low pass filters are applied to the demodulated or downshifted signals. Other filtering may be used.

For the transmit-receive technique, the transmit frequencies from different events are at different frequencies, so the receive signals are also at the different frequencies. For example, half of the transmit beams are centered at 2 MHz and the other half centered at 3 MHz. The receive signals likewise are centered at 2 and 3 MHz, depending on which transmit beam a given receive signal is responsive. Filtering may be applied to reduce noise.

In an alternative embodiment, the ultrasound scanner uses a combination of the receive-only and transmit-receive techniques. The signals received in a given frequency band may be filtered to divide the signals into multiple sub-bands. For example, the transmit-receive technique provides for receive signals in two bands (e.g., 1-3 MHz and 3-5 MHz). The receive-only technique is applied to the signals in one or both of the bands (e.g., 1-3 MHz signals filtered to provide 1-2 MHz and 2-3 MHz sub-bands and 3-5 MHz signals filtered to provide 3-4 MHz and 4-5 MHz sub-bands). For each transmit frequency band, the receive signals are separated into multiple sub-bands. Each of the transmit frequencies are broken up into multiple sub-bands before displacement estimation.

The transmit-receive technique or combination of the transmit-receive and receive-only techniques may more effectively reduce speckle as compared to the receive-only technique since the speckle reduction is inversely proportional to the overlap of the frequency spectra. By having the transmit pulses centered at different frequencies, the spectra can be more different as compared to only filtering the receive signals. Some ultrasound scanners may not be capable of sequencing the transmit beams to have different frequencies through a sequence of tracking transmissions, so rely on the receive-only technique. This receive-only technique may beneficially reduce speckle.

FIG. 2 shows an example sequence of transmit events used for the transmit-receive technique. The pulse sequence is for two-frequency compounding for radiation force-based elasticity imaging. The transmit and receive operations are interleaved. The transmit operations for the different frequencies are interleaved, so the corresponding receive operations for the different frequencies are interleaved.

The ultrasound scanner transmits a sequence of first ultrasound pulses having a first center frequency. In this example, every other transmit pulse has the same first center frequency and/or band. In response to each of these transmit pulses, the ultrasound scanner receives first ultrasound echoes. Echoes are received in response to each transmission, so a sequence of first ultrasound echoes are received interleaved with the transmissions of the first ultrasound pulses. First ultrasound echoes are received for one first ultrasound pulse prior to then transmitting a next of the first ultrasound pulses. In the example of FIG. 2, this transmit event, then receive event for a given frequency band occurs nine times. A receive event occurs in between each transmit event represented by an arrow in FIG. 2, so receipt of the first ultrasound echoes for one event occurs prior to transmission of the next second ultrasound pulse.

The ultrasound scanner also transmits a sequence of second ultrasound pulses at a second center frequency and/or band. The second center frequency is different from the first center frequency. The ultrasound scanner transmits a sequence of the second ultrasound pulses having a second center frequency. In this example, every other transmit pulse has the same second center frequency and/or band. The second ultrasound pulses are transmitted in separate transmit events (i.e., separated by receive events) from each other and the transmit events for the first ultrasound pulses.

In response to each of these second transmit pulses, the ultrasound scanner receives second ultrasound echoes. Echoes are received in response to each second transmission, so a sequence of second ultrasound echoes are received interleaved with the transmissions of the second ultrasound pulses. A sequence of second ultrasound echoes are received for the sequence of second ultrasound pulses. Second ultrasound echoes are received for one second ultrasound pulse prior to then transmitting a next of the second ultrasound pulses. In the example of FIG. 2, this transmit event, then receive event for a given frequency band occurs nine times. A receive event occurs in between each transmit event represented by an arrow in FIG. 2, so receipt of the second ultrasound echoes for one event occurs prior to transmission of the next first ultrasound pulse.

Figure 3:
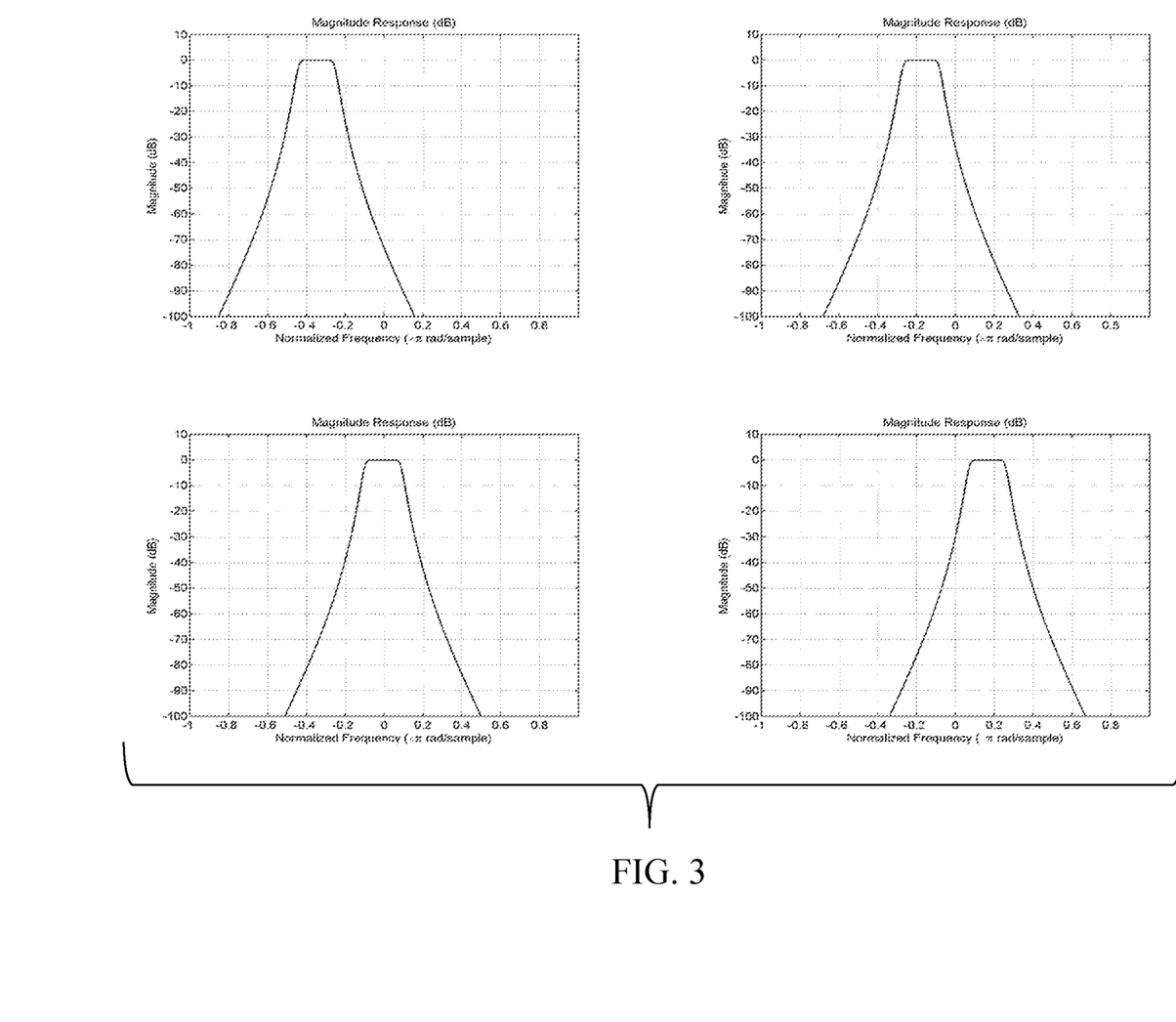
FIG. 3 shows example filters for sub-bands.
Figure 4:
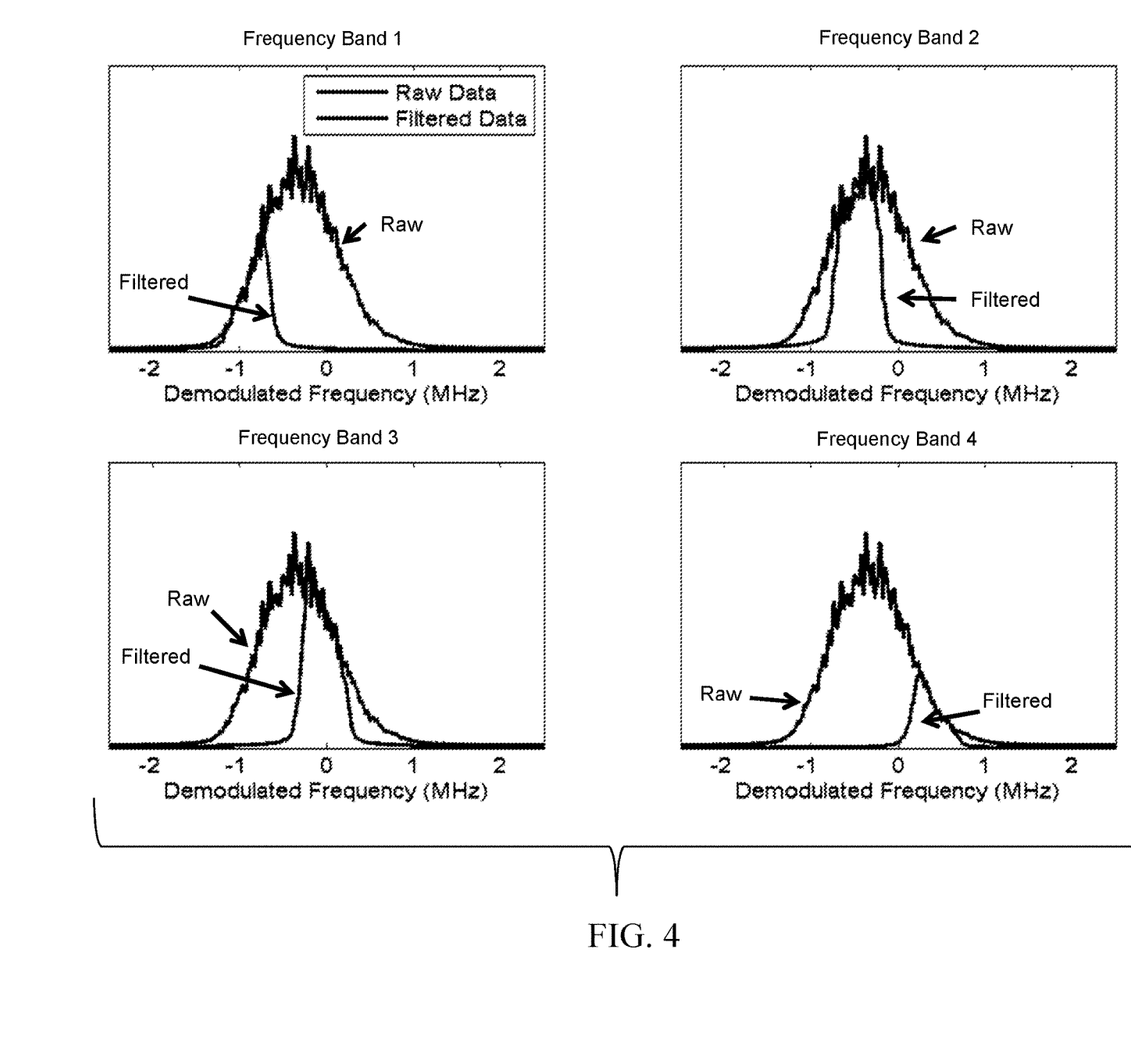
FIG. 4 shows example receive data filtered by the filters of FIG. 3.

FIGS. 3-4 show one embodiment of the receive-only technique. In this example, the ultrasound scanner acquires IQ data by scanning a phantom cylindrical target (imaged in both parallel and perpendicular geometries) and a uniform phantom. The scanning is for shear wave velocity. Complex, low pass filters are applied to the IQ data in order to obtain different frequency spectra for processing. In this example, four complex filters are represented in FIG. 3. These are infinite impulse response (IIR) filters, but finite impulse response (FIR) filters may be used. The center frequencies are shown as normalized values. FIG. 4 shows the frequency spectra of the input IQ data as a light line (raw data). This input data is the same for each of the four filters. The frequency spectra for the IQ data after using the filters of FIG. 3 are shown in FIG. 4 as the dark line in each of the four frequency bands. The resulting filtered frequency spectra are then used to determine displacements.

Returning to FIG. 1, the ultrasound scanner determines tissue motion is detected as a displacement in one, two, or three dimensions. Motion responsive to the applied force, generated shear wave or other wave may be detected. The tissue motion is detected at different times. The different times correspond to the different tracking scans (i.e., transmit and receive event pairs).

Tissue motion is detected by estimating displacement relative to the reference tissue information. For example, the displacement of tissue along scan lines is determined. The displacement may be measured from tissue data, such as B-mode ultrasound data, but flow (e.g., velocity) or IQ information prior to detection may be used.

Correlation, cross-correlation, phase shift estimation, minimum sum of absolute differences or other similarity measure is used to determine the displacement between scans (e.g., between the reference and the current). For example, each IQ data pair is correlated to its corresponding reference to obtain the displacement. Data representing a plurality of spatial locations is correlated with the reference data. As another example, data from a plurality of spatial locations (e.g., along the scan lines) is correlated as a function of time. For each depth or spatial location, a correlation over a plurality of depths or spatial locations (e.g., kernel of 64 depths with the center depth being the point for which the profile is calculated) is performed. The spatial offset with the highest or sufficient correlation at a given time indicates the amount of displacement. For each location, the displacement as a function of time is determined.

Two or three-dimensional displacement in space may be used. One-dimensional displacement along a direction different from the scan lines or beams may be used.

The monitoring is performed for any number of scan lines. For example, four receive beams are formed in response to each transmission. In other embodiments, only a single receive beam or other numbers of receive beams are formed in response to each transmission.

After transmitting the acoustic radiation force to induce displacement, B-mode transmissions are performed repetitively along a single scan line and receptions along four adjacent scan lines. Each repetition monitors the same region or locations for determining tissue response for those locations. By repeating the transmitting of the ultrasound pulses and the receiving of the ultrasound echoes over the time, the displacements over the time are determined. The tracking is repeated. The repetition is for different transmit and receive events. Any number of M repetitions may be used, such as repeating about 50-100 times. The repetitions occur as frequently as possible while the tissue recovers from the stress, but without interfering with reception. The tissue temporal displacement profile is obtained by repeatedly transmitting to and receiving signals from the same target area in a similar way as the Doppler method does.

As the tissue being imaged along the scan lines deforms, the B-mode intensity may vary. For the monitored scan lines, a sequence of data is provided representing a time profile of tissue motion.

The detection of tissue motion occurs while or after the echoes are received. In one embodiment, the received information is stored and may be used for later detection. In other embodiments, the received information is used for detection as the data is received.

The displacements are determined separately for the receive signals at different frequencies. Two or more time sequence of displacements are determined for a given location from the two or more time sequence of received signals at a respective two or more center frequencies or frequency bands. Tissue motion is detected from the signals at the different frequencies. Displacements are estimated for each frequency band. Displacements of the tissue over time are determined separately for the different frequency bands and/or sub-bands, providing different displacement profiles.

For the receive-only technique, a displacement is determined for each time for each frequency. Receive signals at each sample time are provided for each frequency. For the transmit-receive technique, displacements for one frequency are provided at only some of the sample times and displacements for the other frequencies are provided at other times. Interpolation and/or line fitting may be used to provide displacements for the same times. For the combination method, displacements for each sub-band of one transmit frequency band are provided for a sub-set of times (e.g., every even sample time) and displacements for each sub-band of another transmit frequency band are provided for another sub-set of times (e.g., every odd sample time). Interpolation and/or line fitting may be used to provide displacements for the same times.

For frequency compounding, the information from different frequencies is combined. In one embodiment, the combination occurs for the displacements. For each given time, the displacements for that time are averaged, weighted averaged, or otherwise compounded. The averaging occurs for each time, resulting in a displacement profile of frequency-compounded displacements. Other averaging of the displacement profiles from different frequency information may be used. In the transmit-receive technique, interpolation or line fitting synthetically achieves the original pulse repetition frequency by creating displacements for all the times for each of the frequencies, providing a temporally fully-sampled signal. In alternative embodiments, the frequency compounding occurs at a later stage of elasticity imaging as discussed below.

In act 42, the ultrasound scanner generates an image of elasticity. The elasticity and resulting image are based on the tissue motions determined from the information at the different frequencies. Where the displacements calculated using information from different frequencies are compounded, the elasticity estimated from the displacements includes the speckle reduction. Alternatively, different elasticities are estimated from displacements based on the information at the different frequencies, respectively. For frequency compounding, the different elasticities or values derived from the different elasticities (e.g., RGB display values) are averaged or combined. The resulting elasticity includes the speckle reduction. Using either approach, elasticities are output for locations and are based on some combination of displacements from information at different frequency bands and/or center frequencies.

The generation of the image of act 42 is represented as estimating the elasticity in act 44 and creating the image in act 46. Other representations may be used to derive output values used for imaging from the displacements.

In one embodiment of act 44, the time of the occurrence of the peak displacement is used to represent the elasticity of the tissue for that location. The time of the peak displacement in the displacement profile is determined at a plurality of locations and used to estimate a wave velocity, such as in shear wave velocity imaging. A plurality of repetitions of the transmit and receive events in acts 36, 38 provide samples over a period of time.

The peak displacement may be identified by finding a maximum displacement. In an alternative embodiment, a curve is fit to the tissue motion samples. Any curve fitting may be used. For example, a regression is applied. Since the shear wave velocity is linear, a robust linear regression with automated outlier detection may indicate the shear wave velocity. The ultrasound data for all of the sample points in the region of interest is plotted for distance as a function of time or by time and distance. The linear regression is applied to the plot or data, providing a line fit to the data. In another example, a spline interpolation is used. After sorting the data of the profiles, cubic spline interpolation is used to reconstruct the final temporal displacement profile. In other embodiments, a Fourier transform is used. The curve is identified in the frequency domain after removing components at undesired frequencies. The inverse transform provides the time curve.

The peak displacement may be calculated from the curve or temporal profile. The maximum displacement indicates the peak displacement. For shear wave imaging, the temporal profile for a given location indicates detection of the shear wave. A peak in the profile, with or without temporal low pass filtering, indicates the passing of the shear wave front. In an alternative embodiment, a phase relationship between displacement profiles at different locations is used to estimate the velocity without identifying the peak displacement.

The tissue response, such as the peak, may be used as a result. Alternatively, further calculations are performed for the estimation of elasticity. A tissue mechanical property may be characterized as a function of the tissue response. The peak and its temporal location in the temporal displacement profile may be used to characterize tissue's mechanical property, such as strain, strain rate, elasticity, viscosity, impedance, or others.

Shear velocity is obtained by determining a time from generation of the shear wave until detection of the shear wave at a different location. The time and distance to the location determine the velocity. The distance is known from the scan line spacing (i.e., the transmit beam position for generating the shear wave and the receive beam position for detecting the shear wave). The time is known from the relative time between generation and detection of the shear wave. The displacement profile peak or other characteristic of the profile indicates the shear wave.

As another example, a feature is extracted from the temporal profiles. Principle component decomposition may be used. A correlation between the different temporal profiles is performed. The lag associated with the different distances for the different temporal profiles provides the shear velocity. Alternatively, a wavelet analysis may be performed. A wavelet transform is applied to the temporal profiles to identify a peak or other characteristic corresponding to the shear wave. A velocity value is identified from the travel time of the peak to each spatial location.

Other estimates may be performed. The peak displacement, time to reach the peak displacement, velocity of the wave from the ARFI focal point to the location, Young's modulus, or other elasticity values may be used. Any elasticity information may be estimated.

Where the displacements from different frequencies are combined, the frequency compounded displacement profile is used. The peak of this displacement profile is found, or information from displacement profiles from multiple locations are used to estimate the elasticity.

Where the displacements from different frequencies are not combined, the elasticity is estimated separately for the different frequencies. For example, displacement profiles are determined for information from two different frequency bands. Two elasticity values are estimated from the two displacement profiles. The resulting scalar elasticity values or values derived from the elasticities are averaged or otherwise combined to provide an output elasticity. The elasticities responsive to information at different frequency bands or center frequencies are compounded. If the displacement profiles are well characterized, an image may be generated from information for each frequency and combined (e.g., taking the mean of the images) to reduce the speckle noise.

Figure 5:
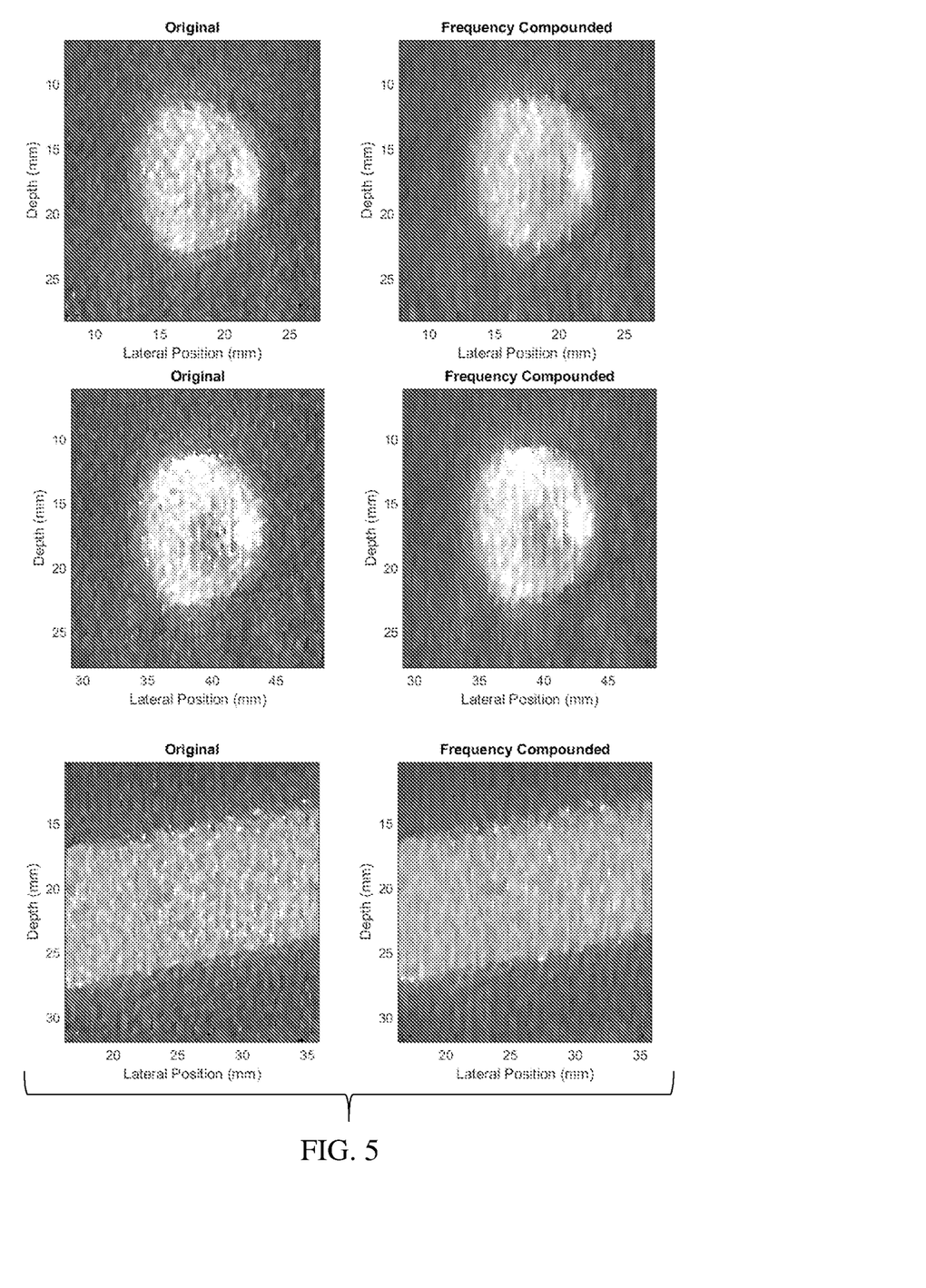
FIG. 5 shows example shear velocity images based on the received data of FIG. 4 with and without the filtering of FIG. 4.
Figure 6:
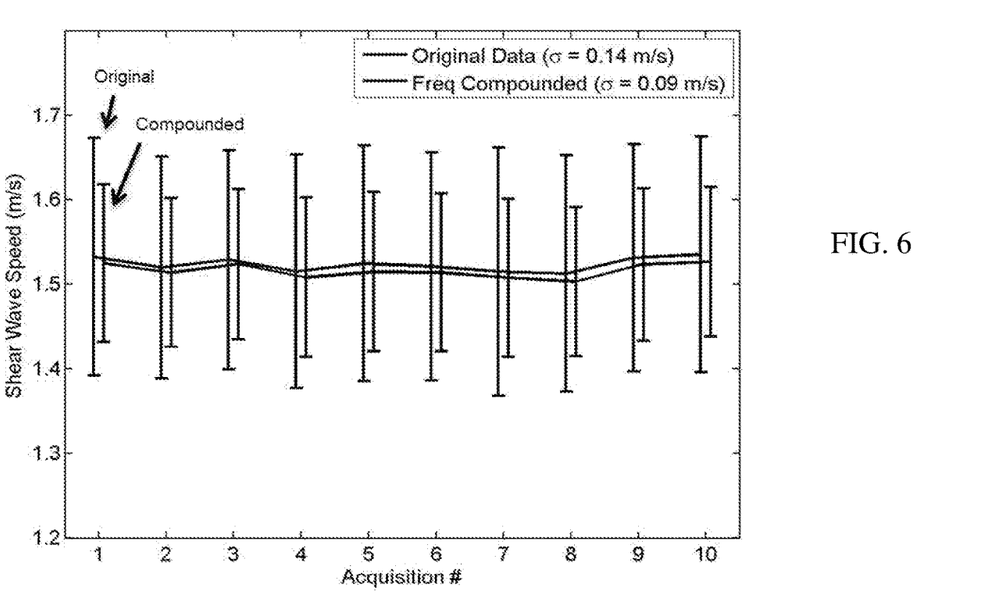
FIG. 6 shows variance in shear wave speed with and without frequency compounding.

FIGS. 5 and 6 show an example of separately processing the data from each frequency band to create separate shear velocity images for each frequency and then compounding the results. The examples of FIGS. 5 and 6 use the IQ data and receive-only technique of FIGS. 3-4. After estimating the shear velocity from data of each frequency band, the median value between the bands is obtained at each spatial location. Example lesion target images of are shown in FIG. 5. The lesions are sloping cylinder targets in a phantom in this example. Two different stiffness targets are show in cross-section (top, middle), and the top target is shown parallel to the cylinder (bottom). The left images correspond to the shear velocity estimation without frequency compounding, and the right images correspond to the frequency compounded images. Spatial filtering may be applied to these images, but is omitted to demonstrate the impact of speckle noise.

For FIG. 6, the same processing is applied to the data collected in the uniform phantom. In this case, 10 acquisitions are performed at different spatial locations throughout the phantom. The mean and standard deviation over the 2D shear velocity image are presented. The error bars indicate the standard deviation of the shear wave speed over the two-dimensional image. In the uniform phantom, there is a 34% reduction in the standard deviation across the image.

To create a spatial image in act 46, the elasticities at different locations are estimated in act 44. The transmitting of the ultrasound pulses, the receiving of the ultrasound echoes over the time, the determining of displacements, and the estimating for different spatial locations is repeated. The resulting estimates of elasticity for different locations are used to generate an elasticity image representing elasticity along one, two, or three dimensions. The output elasticity for the different spatial locations is used in elasticity imaging.

The transmission of the ARFI pulse may or may not be repeated. To monitor a larger region, additional receive beams may be formed in response to the monitoring transmit beam. Alternatively, another ARFI pulse is transmitted and the transmit beams and receive beams are provided at a different spatial locations. In a 6 mm×10 mm monitoring region example, 36 receive scan lines may be provided. At four receive beams per transmit beam, the process is repeated for different lateral spacing nine times. For each receive beam location, a time profile of motion information is provided, represented by the ultrasound data.

The samples may be acquired for one depth. Alternatively, the sampling may be arranged to provide one gate covering the entire axial extent of the region of interest. In another embodiment, samples are obtained at multiple depths for each receive beam. A separate time profile is provided for each axial depth as well as lateral location. Any number of depths may be used, such as about 200 samples for 5 mm or 400 samples for 10 mm.

Ultrasound data representing different locations in the region of interest is obtained. The ultrasound data is obtained in real-time with the scanning or obtained from a memory. Tissue motion for each location is determined as a function of time. For each location, the motion information represents the response at different times, providing a temporal profile. Other scanning, monitoring, or techniques may be used to obtain ultrasound data to estimate an elasticity image.

In act 46, the ultrasound scanner generates an image of output elasticities. In one embodiment, the image is a shear wave velocity image. The shear wave velocity as a function of location is output. Other elasticity information may be used. In alternative or additional embodiments, the elasticity is output as a value (e.g., shear wave velocity for a selected point). A graph, table, or chart of elasticities may be output as the image. Due to the frequency compounding, any one, two, or three-dimensional rendering may include less speckle noise. Due to the frequency compounding, any value, such as in a graph, may have greater precision.

FIG. 7 shows one embodiment of a system 10 for noise reduction in acoustic radiation force impulse imaging. Frequency compounding is used to reduce speckle in ARFI-based elasticity imaging, such as in shear wave imaging. The system 10 implements the method of FIG. 1 or other methods.

The system 10 is a medical diagnostic ultrasound imaging system or ultrasound scanner. In alternative embodiments, the system 10 is a personal computer, workstation, PACS station, or other arrangement at a same location or distributed over a network for real-time or post acquisition imaging, so may not include the beamformers 12, 16 and transducer 14.

The system 10 includes a transmit beamformer 12, a transducer 14, a receive beamformer 16, an image processor 18, a display 20, a memory 22, and a filter 24. Additional, different or fewer components may be provided. For example, a user input is provided for manual or assisted selection of display maps, selection of tissue properties to be determined, region of interest selection, selection of transmit sequences, or other control.

The transmit beamformer 12 is an ultrasound transmitter, memory, pulser, analog circuit, digital circuit, or combinations thereof. The transmit beamformer 12 is configurable to generate waveforms for a plurality of channels with different or relative amplitudes, delays, and/or phasing.

The transmit beamformer 12 generates and causes transmission of pulses having a center frequency and bandwidth. A single band with just one center frequency is used for any given transmission. Rather than using frequency coding, the spectra for a given transmission has a single peak, such as at the center frequency with no peaks within 20 dB of the single peak. Other peaks may be provided due to implementation of the waveform generator, but the other peaks lack sufficient power to be within 20 dB of the center frequency peak, so there is a single peak.

The transmit beamformer 12 is configured to transmit a sequence of pulses. Using a programmable waveform generator, memory, pulser control, or other device, the number of cycles, type of waveform, frequency, or other characteristics establishing the center frequency and bandwidth are set. For a given pulse or transmit beam, the transmit beamformer 12 generates the pulse as having a single center frequency, such as a spectra having one peak within 20 dB down from that peak. The pulse forms the transmit event for a responsive receive operation.

In one embodiment, the same pulse is generated repetitively with gaps in time for receive operation after each pulse. Each pulse of the sequence is the same, at least in center frequency and/or frequency band and given tolerance for the hardware. The center frequency and frequency band for different transmissions is the same for other transmissions. In another embodiment, the control, buffering, or programming is altered for each pulse, by group of pulses or other repetition step to transmit pulses with different center frequencies and/or frequency bands. For example, one pulse is transmitted at one center frequency, then the transmit beamformer 12 is re-configured (e.g., during the receive event) so that the next pulse is transmitted at a different center frequency. The transmit beamformer 12 is configured to transmit the pulses in a sequence with the single band and center frequency of each pulse switching between the different frequency bands through the sequence.

Upon transmission of acoustic waves from the transducer 14 in response to the generated waves, one or more beams are formed. For elasticity imaging, the same region is scanned multiple times. In Doppler imaging and elasticity estimation, the sequence may include multiple beams along a same scan line before scanning an adjacent scan line. An ARFI transmission may be generated by the transmit beamformer 12 as part of the sequence. By repeating the elasticity estimation process for different locations, sequences of transmit beams are generated to scan a two or three-dimensional region. Sector, vector, linear, or other scan formats may be used. The transmit beamformer 12 may generate a plane wave or diverging wave for more rapid scanning.

The transmit beams are formed at different energy or amplitude levels. Amplifiers for each channel and/or aperture size control the amplitude of the transmitted beam. The ARFI transmit beams may have greater amplitudes than for imaging or detecting tissue motion. Alternatively or additionally, the number of cycles in the ARFI pulse or waveform used is typically greater than the pulse used for tracking (e.g., 100 or more cycles for ARFI and 1-6 cycles for tracking).

The transducer 14 is a 1-, 1.25-, 1.5-, 1.75-, or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer. The elements connect with channels of the transmit and receive beamformers 12, 16.

The transmit beamformer 12 and receive beamformer 16 connect with the same elements of the transducer 14 through a transmit/receive switch or multiplexer. The elements are shared for both transmit and receive events. One or more elements may not be shared, such as where the transmit and receive apertures are different (only overlap or use entirely different elements).

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to a transmission. In alternative embodiments, the receive beamformer 16 is a processor for generating samples using Fourier or other transforms. The receive beamformer 16 may include channels for parallel receive beamforming, such as forming two or more receive beams in response to each transmit event. The receive beamformer 16 outputs beam summed data, such as IQ values, for each beam.

The receive beamformer 16 operates during gaps in the sequence of transmit events. By interleaving receipt of signals with the transmit pulses, a sequence of receive beams are formed in response to the sequence of transmit beams. After each transmit pulse and before the next transmit pulse, the receive beamformer 16 receives signals from acoustic echoes. Dead time during which receive and transmit operations do not occur may be interleaved to allow for reverberation reduction.

The receive beamformer 16 outputs beam summed data representing spatial locations at a given time. Data for a single location, locations along a line, locations for an area, or locations for a volume are output. Dynamic focusing may be provided. The data may be for different purposes. For example, different scans are performed for B-mode or tissue data than for shear wave velocity estimation. Data received for B-mode or other imaging may be used for estimation of the elasticity image. The shear wave at locations spaced from a focus of the pushing pulse or the tissue response at the focus are monitored to determine elasticity.

The receive beamformer 16 may include the filter 24. Alternatively, the filter 24 is a separate component. The filter 24 may be positioned to filter beamformed data output by the receive beamformer 16, to filter radio frequency data input to the receive beamformer 16, or to filter other data at other points along the ultrasound processing.

The filter 24 isolates information at desired frequency bands and/or reduces the contribution of information at frequencies outside the desired frequency band. The filter 24 is a band pass filter or demodulator and band or low pass filter. Discrete hardware (e.g., resistors, capacitors, inductors, buffers, multipliers, and/or summers) may be used. Alternatively, a processor implements the filter 24. The filter 24 may include parallel paths for filtering the same receive signals or beamformed data into different frequency bands or sub-bands. The filter 24 is programmable or is a bank of separate filters for filtering to pass different frequency bands and/or center frequencies.

The filter 24 outputs information in different frequency bands for the received signals. In one embodiment, the same receive signals are filtered into different sub-bands or frequency bands. For each receive event, the same filtering is applied. In an alternative or additional embodiment, the receive signals responsive to different transmit events are filtered differently. The receive filtering matches the transmit center frequency and/or frequency band, so varies where the transmit pulses vary in frequency through the sequence.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, network, server, group of processors, data path, combinations thereof or other now known or later developed device for detecting and processing information for display from beamformed ultrasound samples. In one embodiment, the processor 18 includes one or more detectors and a separate processor. The processor 18 performs any combination of one or more of the acts 40-46 shown in FIG. 1.

The beamformed data is provided in two or more different frequency bands and/or having two or more center frequencies. Prior to or after detection, the processor 18 is configured to detect displacements of tissue responding to acoustic radiation force from the information in the different frequency bands and/or center frequencies. In the receive-only technique, the processor 18 detects more than one displacement for each time and location, such as a displacement for each of the different frequencies. In the transmit-receive technique, the processor 18 detects one displacement for each time, but the displacements for different times are from information at different frequencies than some of the other times (e.g., every other time is of one frequency and the other times are of another frequency).

The processor 18 detects the displacement using correlation or other measure of similarity. By spatially offsetting a tracking set of data relative to a reference set of data in one, two, or three-dimensional space, the offset with the greatest similarity indicates the displacement of the tissue. Other displacement detection may be used. A displacement profile or displacement over time may be created.

The processor 18 is configured to estimate elasticity. For each spatial location sampled in tracking, the processor 18 determines a mechanical property of tissue or characteristic of the wave propagation at that location. For example, the shear wave velocity is calculated. The relative phase in the displacement profiles from an adjacent location and/or timing of peak in the displacement profile at the location of interest is identified and used with the geometry of the location relative to the shear wave origin and timing of the shear wave generation to calculate the velocity.

Frequency compounding in the elasticity imaging is implemented by the processor 18. In one embodiment, the displacements associated with information in the different frequencies are combined. For example, displacements for the same location and time but from information at different frequencies are averaged. As another example, curve fitting or interpolation are used to generate information from different frequencies at the same time or sampling. The displacements for the same time but from information at different frequencies are averaged.

In another embodiment, the processor 18 estimates the elasticity for each location and for each frequency. The scalar elasticities or display values from the information at the different frequencies are then averaged or otherwise combined.

In either approach, the processor 18 outputs an elasticity for each of one or more locations. The elasticity is from a frequency compounding, so has reduced speckle noise.

The processor 18 generates display data, such as graphic overlays and images. The display data is in any format, such as values before mapping, gray scale or color-mapped values, red-green-blue (RGB) values, scan format data, display or Cartesian coordinate format data, or other data. The processor 18 outputs elasticity appropriate for the display device 20.

The display device 20 is a CRT, LCD, projector, plasma, printer, or other display for displaying elasticity (e.g., shear velocity), graphics, user interface, validation indication, two-dimensional images, or three-dimensional representations. The display device 20 displays ultrasound images, the elasticity, and/or other information. For example, the display 20 outputs tissue response information, such as a one, two, or three-dimensional representation of the elasticity. Elasticities for different spatial locations form an image. Other images may be output as well, such as overlaying the elasticity as a color-coded modulation on a gray scale B-mode image.

In one embodiment, the display device 20 outputs an image of a region of the patient, such as a two-dimensional elasticity, Doppler tissue, or B-mode image. The image includes a location indicator for the elasticity. The location relative to the imaged tissue for which an elasticity value is calculated is shown. The elasticity is provided as an alphanumeric value on or adjacent the image of the region. The image may be of the alphanumeric value with or without spatial representation of the patient. Alternatively or additionally, elasticity is determined for a plurality of locations and the image pixels are modulated as a function of the elasticity for spatially representing shear velocity.

The processor 18 operates pursuant to instructions stored in the memory 22 or another memory. The memory 22 is a computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for noise reduction in elasticity imaging with an ultrasound scanner, the method comprising:

transmitting acoustic radiation force from a transducer of the ultrasound scanner as a single pushing pulse to tissue of a patient, the tissue responding to stress caused by the acoustic radiation force of the single pushing pulse;

transmitting, by the ultrasound scanner, a sequence of tracking transmit beams in a sequence of transmit events, each transmit beam having a frequency response with a single peak;

receiving, by the ultrasound scanner, a sequence of tracking receive signals, each tracking receive signal of the sequence being a receive event in response to respective one of the transmit beams, the receive events for receiving of the tracking receive signals interleaved with the transmit events for transmitting of the transmit beams, the sequence of the tracking receive signals received over a period while the tissue responds to the stress caused by the acoustic radiation force of the single pushing pulse;

providing the tracking receive signals at different frequency bands; then determining, by the ultrasound scanner, tissue motion for each of the different frequency bands from the tracking receive signals at the different frequency bands and received during the period while the tissue responds to the stress caused by the acoustic radiation force of the single pushing pulse; and generating, by the ultrasound scanner, an image of elasticity, the image being based on the tissue motions at the different frequency bands.

2. The method of claim 1 wherein the transmitting the sequence comprises transmitting with the transmit beams comprising a repeating pattern of the different frequency bands, wherein the receiving comprises receiving the tracking receive signals at the different frequency bands, and wherein the tissue motions of the different frequency bands are displacements detected at the different frequency bands.

3. The method of claim 2 wherein the receiving comprises filtering the tracking receive signals into multiple sub-bands for each of the different frequency bands, and wherein the displacements are detected at the different sub-bands of the different frequency bands.

4. The method of claim 1 wherein the transmitting the sequence comprises transmitting with the transmit beams all having a same center frequency, and wherein receiving comprises filtering the tracking receive signals into the different frequency bands.

5. The method of claim 1 wherein the generating the image comprises generating different elasticities for the different frequency bands and combining the different elasticities, the image being of the combined elasticities.

6. The method of claim 1 wherein the generating the image comprises combining the tissue motions at the different frequency bands and estimating the elasticity from the combined tissue motion.

* * * * *